(12) United States Patent
Lee et al.

(10) Patent No.: US 8,233,686 B2
(45) Date of Patent: Jul. 31, 2012

(54) METHODS AND SYSTEMS FOR LOCATING OBJECTS EMBEDDED IN A BODY

(76) Inventors: Junghoon Lee, Baltimore, MD (US);
Jerry L. Prince, Lutherville, MD (US);
Christian Labat, Montreuill (FR);
Everette C. Burdette, Champaign, IL (US)

( * ) Notice: Subject to any disclaimer, the term of this patent is extended or adjusted under 35 U.S.C. 154(b) by 0 days.

(21) Appl. No.: 13/171,034

(22) Filed: Jun. 28, 2011

(65) Prior Publication Data
US 2011/0317810 A1    Dec. 29, 2011

Related U.S. Application Data

(60) Provisional application No. 61/359,106, filed on Jun. 28, 2010.

(51) Int. Cl.
*G06K 9/00* (2006.01)
*G01N 23/04* (2006.01)

(52) U.S. Cl. .......................................... 382/128; 378/62

(58) Field of Classification Search .......... 382/128–134; 378/4, 8, 21–27, 62, 63, 87, 98.12; 600/407, 600/410, 411, 425, 427; 250/390.02; 128/920, 128/922
See application file for complete search history.

(56) References Cited

U.S. PATENT DOCUMENTS
7,136,518 B2 *    11/2006    Griffin et al. ................. 382/133

OTHER PUBLICATIONS

Ameet Jain, et al., C-arm Calibration- Is it Really Necessary?, LNCS, vol. 3749, (2005), pp. 639-646.
Ameet Kumar Jain, FTRAC—A Robust Fluoroscope Tracking Fiducial, Med. Phys., vol. 32, (2005) pp. 3185-3198.
Junghoon Lee, et al.,Reduced-Dimensionality Matching for 3-D Reconstruction of Prostate Brachytherapy Implants from Incomplete Data, IEEE (2009), pp. 1047-1050. (Presented Jul. 1, 2009).
Junghoon Lee, et al. REDMAPS: Reduced-Dimensionality Matching for Prostate Brachytherapy Seed Reconstruction, IEEE Transactions on Medical Imaging, vol. 30, No. 1, Jan. 2011, pp. 38-51.
Junghoon Lee, et al, Optimal Matching for Prostate Brachytherapy Seed Localization with Dimension Reduction, MICCAI, Part 1, LNCS, 5671 (Sep. 20-24, 2009), pp. 59-66.

* cited by examiner

*Primary Examiner* — Abolfazl Tabatabai
(74) *Attorney, Agent, or Firm* — Venable LLP; Henry J. Daley

(57) ABSTRACT

A method of processing image data from an imaging system for locating a plurality N of objects embedded in a body includes receiving data for a first two-dimensional image of a region of interest of the body containing the plurality N of objects, the first two-dimensional image being obtained from a first imaging setting of the imaging system relative to the region of interest; receiving data for a second two-dimensional image of a region of interest of the body containing the plurality N of objects, the second two-dimensional image being obtained from a second imaging setting of the imaging system relative to the region of interest; and receiving data for a third two-dimensional image of a region of interest of the body containing the plurality N of objects, the third two-dimensional image being obtained from a third imaging setting of said imaging system relative to said region of interest.

17 Claims, 4 Drawing Sheets

METHODS AND SYSTEMS FOR LOCATING OBJECTS EMBEDDED IN A BODY

CROSS-REFERENCE OF RELATED APPLICATION

This application claims priority to U.S. Provisional Application No. 61/359,106 filed Jun. 28, 2010, the entire contents of which are hereby incorporated by reference.

This invention was made with Government support of Grant Nos. 5R44CA099374 and 1R01CA151395, awarded by the Department of Health and Human Services, The National Institutes of Health (NIH). The U.S. Government has certain rights in this invention.

BACKGROUND

1. Field of Invention

The field of the currently claimed embodiments of this invention relates to methods and systems for locating objects embedded within a body, and more particularly to methods and systems for locating objects embedded within a body based on reduced computational requirements.

2. Discussion of Related Art

C-arm fluoroscopy is widely used for visual assessment during clinical procedures. However, it is limited in that it cannot show soft tissues or organs of interest and other relevant structures. On the other hand, use of other imaging modalities such as ultrasound during clinical procedures provides real-time visualization of the tissue/organ of interest but does not provide radiographic information. Fusion of these complementary imaging modalities would provide benefits during many procedures.

For example, interventional tool registration with soft tissue would benefit from being able to accurately view the tool and the soft tissue of interest simultaneously during a medical procedure. The procedure could be performed with greater precision through improved tool visualization and registration with the soft tissues undergoing the procedure. Further, the ability to visualize the soft tissue using another imaging modality such as ultrasound provides real time information to the clinician performing the procedure.

Carcinoma of the prostate is one of the most prevalent and fatal cancers in men in North America. Prostate cancer alone accounts for 25% of cancer cases and 9% of cancer deaths in men with approximately 200,000 estimated new cases and 30,000 estimated deaths each year in the United States alone. During the past decade, ultrasound-guided low dose rate (LDR) transperineal brachytherapy has become one of the popular choices of therapy for patients with early prostate cancer. It involves the implantation of radioactive seeds (either $^{125}I$ or $^{103}Pd$) into the prostate in the patient. Brachytherapy involves the placement of radioactive pellets or "seeds" into or adjacent cancerous tissue of a patient. Brachytherapy makes it possible to treat the cancer with a high total dose of radiation in a concentrated area in a short period of time, and at the same time spare healthy tissues the treatment with radiation. The key to successful brachytherapy is the accurate placement of the seeds. However, faulty needle and seed placement often cause an insufficient dose to the cancer and/or inadvertent radiation of healthy tissues. The ability to perform dosimetry optimization during the procedure could change the standard of care in brachytherapy, but such function is not available today and it is unfortunate that implants are currently performed without an explicit dosimetry evaluation in the operating room. Generally, dosimetric analysis requires precise localization of the implanted seeds in relation to the cancerous tissue and surrounding anatomy. Brachytherapy success critically depends on adequately dosing the target gland by implanting a sufficient number and distribution of radioactive seeds while avoiding excessive radiation toxicity to adjacent organs, most notably urethra, bladder, and rectum.

In the contemporary prostate brachytherapy procedure, an implant plan is made either preoperatively or intraoperatively based on transrectal ultrasound (TRUS) imaging. The physician first contours the prostate and the planning target volume from ultrasound images acquired from TRUS probe, and then a treatment planning system is used to create a seed implant plan to deliver the prescribed dose to the target. During the implant procedure, the patient lies on his back with his legs in a high lithotomy position. The physician places the seeds into the planned locations in the prostate via needles inserted transperineally through a template guide using TRUS guidance as depicted in FIG. 1.

One of the greatest challenges of the current TRUS-guided implant method is that it is difficult to visualize the implanted seeds on TRUS. Seed positions may be estimated intraoperatively at the time of deposition based on visualization of the needle tip on TRUS images, but this method is subject to inaccuracies due to procedural variations such as patient motion, needle deviation, seed migration, and prostatic edema. As a consequence, seed positioning variations cannot be identified intraoperatively during the procedure. An additional seed implant session (which can be technically challenging) or supplemental external beam radiation is sometimes necessary to cover underdosed regions. The future direction of prostate brachytherapy involves the development of a system that intraoperatively assists the brachytherapist to achieve optimal dosimetric quality with a favorable dose profile to the target and surrounding normal tissues.

In order to achieve concurrent visualization of the anatomy and implanted seeds, systems that use ultrasound imaging and x-ray fluoroscopy have been proposed to permit both monitoring of the implant process and reconstruction of the implanted seeds for intraoperative treatment optimization. In particular, x-ray projection images can be acquired using conventional mobile c-arms and the three-dimensional (3-D) seed positions can be reconstructed from these data. The reconstructed seeds can then be registered to the prostate volume that is visualized using the TRUS images. Overall, this process provides sufficient information for the computation of an intraoperative dose distribution at intermediate implant stages in relation to the target from which a modification to the original seed placement plan can be computed and carried out during the same therapeutic procedure.

There has been extensive previous work on the reconstruction of brachytherapy seeds from multiple x-ray images. The most common approaches consist of the following tasks: (1) acquire several x-ray images from different orientations; (2) segment the seeds and find their two-dimensional (2-D) coordinates in every image; (3) determine which segmented seeds in each image correspond to the same physical seed ("seed matching"); and (4) compute the positions of each physical seed from the corresponding seeds ("triangulation"). In order to minimize the chances of having multiple, equally-valid solutions to this problem, at least three images are required. Regardless of the number of acquired images, the resulting optimization problem required for seed matching is computationally very expensive due to combinatorial explosion, which implies that most reconstruction algorithms must be approximate since carrying out an exhaustive search is too time-consuming for routine clinical practice. Most of the current approaches assume that every seed can be individually identified in every image; but, in reality, each image will generally contain some seeds whose projections overlap. Both the computational demands and the so-called "hidden seed problem" represent significant impediments to the routine application of currently known seed reconstruction methods in clinical practice.

In recent years, several methods have been proposed for solving the hidden seed problem. The use of a statistical classifier was explored to determine the number of seeds in a self-connected region in the segmented seed images, but it was prone to generate false positives or negatives that can critically influence the following reconstruction. There was an epipolar geometry-constrained pseudo-seed-matching strategy, but it requires a co-planar imaging constraint in order to use three images since epipolar geometry is defined only over two projections. There are tomosynthesis-based implant reconstruction methods, but these methods generally require a much larger number of images and wider image acquisition angles than seed-matching approaches for stable implant reconstruction, and are slow because the whole volume has to be reconstructed. The use of adaptive grouping techniques were also used in order to divide the seed images into groups for efficient seed reconstruction, but these methods have overdividing problems due to incorrect division of triplets (when three images are used), resulting in false positive seeds in the reconstruction.

In summary, existing seed reconstruction methods have at least one of the following fundamental limitations: (1) they are sensitive to pose errors of the imaging device, (2) they cannot resolve the hidden seed problem, (3) they require a large number of images, large image acquisition angles, and a long time to compute a converging solution, and (4) they require constrained motion of the imaging device, e.g., isocentric circular trajectory.

There thus remains the need for improved methods and systems for locating objects embedded within a body.

SUMMARY

A method of processing image data from an imaging system for locating a plurality N of objects embedded in a body according to an embodiment of the current invention includes receiving data for a first two-dimensional image of a region of interest of the body containing the plurality N of objects, the first two-dimensional image being obtained from a first imaging setting of the imaging system relative to the region of interest; receiving data for a second two-dimensional image of a region of interest of the body containing the plurality N of objects, the second two-dimensional image being obtained from a second imaging setting of the imaging system relative to the region of interest; and receiving data for a third two-dimensional image of a region of interest of the body containing the plurality N of objects, the third two-dimensional image being obtained from a third imaging setting of said imaging system relative to said region of interest. The method further includes determining two-dimensional positions for a first plurality of objects $N_1$ in the first two-dimensional image, each of the first plurality of objects $N_1$ corresponding to at least one of the plurality N of objects; determining two-dimensional positions for a second plurality of objects $N_2$ in the second two-dimensional image, each of the second plurality of objects $N_2$ corresponding to at least one of the plurality N of objects; determining two-dimensional positions for a third plurality of objects $N_3$ in the third two-dimensional image, each of the third plurality of objects $N_3$ corresponding to at least one of the plurality N of objects; calculating a cost associated with each of the first plurality of objects $N_1$ paired with each of the second plurality of objects $N_2$ to provide $N_1 \times N_2$ pair combinations, each said cost being indicative of a likelihood of a correct pairing; eliminating some of the $N_1 \times N_2$ pair combinations from further calculations based on a predetermined threshold to result in a reduced number $n_1$ of remaining pairs for further calculations, $n_1$ being less than $N_1 \times N_2$; calculating a cost associated with each of the $n_1$ pairs and each of the third plurality of objects $N_3$ to provide $n_1 \times N_3$ triplet combinations, each said cost being indicative of a likelihood of a correct triplet matching; eliminating some of the $n_1 \times N_3$ triplet combinations from further calculations based on the predetermined threshold to result in a reduced number $n_2$ of remaining triplets, $n_2$ being less than $n_1 \times N_3$; and calculating three-dimensional positions of each of the plurality N of objects embedded in the region of interest of the body based on surviving matches of objects in each two-dimensional image. The first, second and third imaging settings all are different from each other.

A computer-readable medium according to an embodiment of the current invention includes software for processing image data from an imaging system for locating a plurality N of objects embedded in a body, which software when executed by a computer causes the computer to receive data for a first two-dimensional image of a region of interest of the body containing the plurality N of objects, the first two-dimensional image being obtained from a first imaging setting of the imaging system relative to said region of interest; receive data for a second two-dimensional image of a region of interest of the body containing the plurality N of objects, the second two-dimensional image being obtained from a second imaging setting of the imaging system relative to the region of interest; and receive data for a third two-dimensional image of a region of interest of the body containing the plurality N of objects, the third two-dimensional image being obtained from a third imaging setting of the imaging system relative to the region of interest. The software when executed by the computer further causes the computer to determine two-dimensional positions for a first plurality of objects $N_1$ in the first two-dimensional image, each of the first plurality of objects $N_1$ corresponding to at least one of the plurality N of objects; determine two-dimensional positions for a second plurality of objects $N_2$ in the second two-dimensional image, each of the second plurality of objects $N_2$ corresponding to at least one of the plurality N of objects; determine two-dimensional positions for a third plurality of objects $N_3$ in the third two-dimensional image, each of the third plurality of objects $N_3$ corresponding to at least one of the plurality N of objects; calculate a cost associated with each of the first plurality of objects $N_1$ paired with each of the second plurality of objects $N_2$ to provide $N_1 \times N_2$ pair combinations, each said cost being indicative of a likelihood of a correct pairing; eliminate some of the $N_1 \times N_2$ pair combinations from further calculations based on a predetermined threshold to result in a reduced number $n_1$ of remaining pairs for further calculations, $n_1$ being less than $N_1 \times N_2$; calculate a cost associated with each of the $n_1$ pairs and each of the third plurality of objects $N_3$ to provide $n_1 \times N_3$ triplet combinations, each said cost being indicative of a likelihood of a correct triplet matching; eliminate some of the $n_1 \times N_3$ triplet combinations from further calculations based on the predetermined threshold to result in a reduced number $n_2$ of remaining triplets, $n_2$ being less than $n_1 \times N_3$; and calculate three-dimensional positions of each of the plurality N of objects embedded in the region of interest of the body based on surviving matches of objects in each said two-dimensional image. The first, second and third imaging settings all are different from each other.

An imaging system for locating a plurality N of objects embedded in a body according to an embodiment of the current invention includes an illumination system; a detection system arranged to form two-dimensional images of a region of interest containing the plurality N of objects embedded in the body; and a data processor encoded with software for processing image data from a detection system. The software, when executed by a computer, causes the computer to receive data for a first two-dimensional image of a region of interest of the body containing the plurality N of objects, the first two-dimensional image being obtained from a first imaging setting of the imaging system relative to said region of interest; receive data for a second two-dimensional image of a region of interest of the body containing the plurality N of objects, the second two-dimensional image being obtained from a second imaging setting of the imaging system relative to the region of interest; and receive data for a third two-dimensional image of a region of interest of the body containing the plurality N of objects, the third two-dimensional image being obtained from a third imaging setting of the imaging system relative to the region of interest. The software when executed by the computer further causes the computer to determine two-dimensional positions for a first plurality of objects $N_1$ in the first two-dimensional image, each of the first plurality of objects $N_1$ corresponding to at least one of the plurality N of objects; determine two-dimensional positions for a second plurality of objects $N_2$ in the second two-dimensional image, each of the second plurality of objects $N_2$ corresponding to at least one of the plurality N of objects; determine two-dimensional positions for a third plurality of objects $N_3$ in the third two-dimensional image, each of the third plurality of objects $N_3$ corresponding to at least one of the plurality N of objects; calculate a cost associated with each of the first plurality of objects $N_1$ paired with each of the second plurality of objects $N_2$ to provide $N_1 \times N_2$ pair combinations, each said cost being indicative of a likelihood of a correct pairing; eliminate some of the $N_1 \times N_2$ pair combinations from further calculations based on a predetermined threshold to result in a reduced number $n_1$ of remaining pairs for further calculations, $n_1$ being less than $N_1 \times N_2$; calculate a cost associated with each of the $n_1$ pairs and each of the third plurality of objects $N_3$ to provide $n_1 \times N_3$ triplet combinations, each said cost being indicative of a likelihood of a correct triplet matching; eliminate some of the $n_1 \times N_3$ triplet combinations from further calculations based on the predetermined threshold to result in a reduced number $n_2$ of remaining triplets, $n_2$ being less than $n_1 \times N_3$; and calculate three-dimensional positions of each of the plurality N of objects embedded in the region of interest of the body based on surviving matches of objects in each said two-dimensional image. The first, second and third imaging settings all are different from each other.

BRIEF DESCRIPTION OF THE DRAWINGS

Further objectives and advantages will become apparent from a consideration of the description, drawings, and examples.

DETAILED DESCRIPTION

Figure 1:
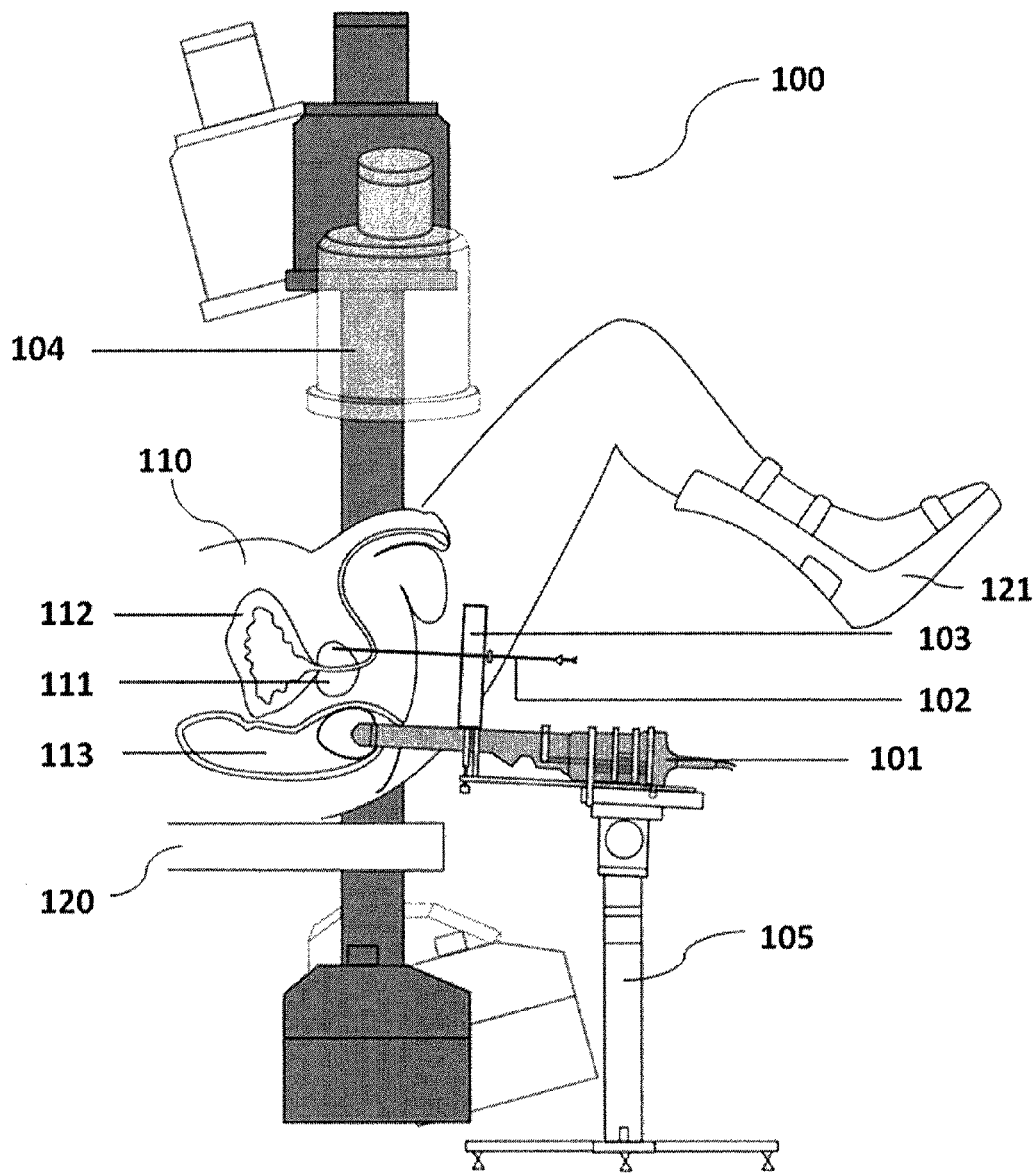
FIG. 1 is an illustration of an example of a fluoroscopy-based prostate brachytherapy implant imaging system according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

Some embodiments of the current invention are directed to 3-D reconstruction and localization of radioactive implants from a limited number of x-ray images taken within limited angles for the purposes of providing real-time monitoring and optimization of medical procedures such as transperineal low-dose rate brachytherapy.

As described herein, the relative pose of a c-arm fluoroscopy image is estimated by registering the fluoroscopy image to a fiducial or marker image. As used herein, the terms "marker" and "seed" are interchangeable and refer to a feature in a material that may be resolved with an imaging technology. Markers or seeds may include a feature already present in the material, such as an inherent part of the material, a feature implanted in the material, a feature attached or fixed to the material, or combinations thereof. Markers or seeds may be man-made or naturally occurring. For example, a marker may be a radioactive seed as used during a brachytherapy procedure, a surgical clip, or any other suitable material or device.

One application of the embodiments described herein is in brachytherapy. Brachytherapy may be performed with ultrasound guidance that provides real-time visualization of the tissue and/or organ of interest but not of the implanted seeds. C-arm fluoroscopy, on the other hand, may be used for visual assessment of the implanted seeds but it does not show the tissue or organ and other relevant structures. Fusion of these complementary modalities can enable dynamic dosimetry. For fusion of these modalities, 3D reconstruction of the seeds is necessary and requires that the relative poses of the fluoroscopy images must be known prior to reconstruction. Some embodiments described herein can provide accurate reconstruction of brachytherapy seed placement, but the general concepts of the current invention are not limited to this example.

More generally, a method of processing image data from an imaging system for locating a plurality N of objects embedded in a body according to the current invention includes receiving data for a first two-dimensional image of a region of interest of the body containing the plurality N of objects, the first two-dimensional image being obtained from a first imaging setting of the imaging system relative to the region of interest; receiving data for a second two-dimensional image of a region of interest of the body containing the plurality N of objects, the second two-dimensional image being obtained from a second imaging setting of the imaging system relative to the region of interest; receiving data for a third two-dimensional image of a region of interest of the body containing the plurality N of objects, the third two-dimensional image being obtained from a third imaging setting of the imaging system relative to the region of interest; determining two-dimensional positions for a first plurality of objects $N_1$ in the first two-dimensional image, each of the first plurality of objects $N_1$ corresponding to at least one of the plurality N of objects; determining two-dimensional positions for a second plurality of objects $N_2$ in the second two-dimensional image, each of the second plurality of objects $N_2$ corresponding to at least one of the plurality N of objects; determining two-dimensional positions for a third plurality of objects $N_3$ in the third two-dimensional image, each of the third plurality of objects $N_3$ corresponding to at least one of the plurality N of objects. The method according to this embodiment of the current invention also includes calculating a cost associated with each of the first plurality of objects $N_1$ paired with each of the second plurality of objects $N_2$ to provide $N_1 \times N_2$ pair combinations, each cost being indicative of a likelihood of a correct pairing; eliminating some of the $N_1 \times N_2$ pair combinations from further calculations based on a predetermined threshold to result in a reduced number $n_1$ of remaining pairs for further calculations, $n_1$ being less than $N_1 \times N_2$; calculating a cost associated with each of the $n_1$ pairs and each of the third plurality of objects $N_3$ to provide $n_1 \times N_3$ triplet combinations, each cost being indicative of a likelihood of a correct triplet matching; eliminating some of the $n_1 \times N_3$ triplet combinations from further calculations based on the predetermined threshold to result in a reduced number $n_2$ of remaining triplets, $n_2$ being less than $n_1 \times N_3$; and calculating three-dimensional positions of each of the plurality N of objects embedded in the region of interest of the body based on surviving matches of objects in each two-dimensional image. The first, second and third imaging settings all are different from each other.

The body can be a human or animal body, but can also be tissue or even some other inanimate body. The objects that are imbedded in the body can be small point-like objects on the scale of the images, but could also be a reference point, such as a center point, of an extended object in other embodiments of the current invention. In some embodiments, the number of objects N can be large, such as greater than 10, or greater than 50, or greater than 100, for example.

The methods of processing image data according to some embodiments of the current invention are not limited to only three two-dimensional images. For example, four, five, six or even a greater number of two-dimensional images can be used to determine the location of the embedded objects according to some embodiments of the current invention. The general concepts of the current invention are not limited to a particular number of two-dimensional images, as long as there are at least three to allow triangulation in three-dimensional space. For example, in the case of four two-dimensional images, the method further includes receiving data for a fourth two-dimensional image of a region of interest of the body containing the plurality N of objects, the fourth two-dimensional image being obtained from a fourth imaging setting of the imaging system relative to the region of interest; determining two-dimensional positions for a fourth plurality of objects $N_4$ in the fourth two-dimensional image, each of the fourth plurality of objects $N_4$ corresponding to at least one of the plurality N of objects; calculating a cost associated with each of the $n_2$ triplets and each of the fourth plurality of objects $N_4$ to provide $n_2 \times N_4$ quartet combinations, each cost being indicative of a likelihood of a correct quartet matching; eliminating some of the $n_2 \times N_4$ triplet combinations from further calculations based on the predetermined threshold to result in a reduced number $n_3$ of remaining quartets, $n_3$ being less than $n_2 \times N_4$; and calculating three-dimensional positions of each of the plurality N of objects embedded in the region of interest of the body based on surviving matches of objects in each the two-dimensional images. The first, second, third and fourth imaging settings all are different from each other. This concept can be extended to five, six, or even more two-dimensional images within the general concepts of the current invention.

According to some embodiments of the current invention, the threshold can be selected based on known properties of the imaging system. For example, the known properties of the imaging system can include known measurement precision. The known properties of the imaging system can also include positioning precision.

In some embodiments of the current invention, the cost can be a function of distance of closest approach of lines extending from a corresponding two-dimensional position to an imaging source direction, for example. The term cost, or cost function, is intended to have a general meaning within the concepts of optimizing methods.

FIG. 1 shows an example of system 100 for TRUS and c-arm fluoroscopy based prostate brachytherapy procedures that can utilize methods according to some embodiments of the current invention. The system 100 can be connected to a data processor, and/or include a built in data processor that includes software according to the current invention. Alternatively, the system 100 could be "hard-wired" to perform methods according to some embodiments of the current invention. The system 100 utilizes commercially available TRUS and x-ray imaging devices such as c-arm fluoroscopy 104 hardware systems in this example. During the implantation procedure, TRUS imaging probe 101 is mounted to the TRUS stepper stand 105, and the surgeon implants radioactive sources into the prostate 111 via needle 102 with transperineal template guide 103. Patient 110 lies on his back on the surgical table 120 with his legs in a high lithotomy position with leg supports 121. The implantation procedure is guided by TRUS, and the x-ray images are acquired using a mobile c-arm when the surgeon needs to evaluate the implantation and update the implant plan in order to adequately eradicate the target gland 111 while avoiding excessive radiation toxicity to adjacent organs, most notably urethra, bladder 112, and rectum 113.

Most mobile c-arms currently available in hospitals use an x-ray image intensifier (XRII) detector, and therefore acquired images show a significant amount of nonlinear geometric distortion and nonuniform intensity distortion that vary with pose, time, and location. The acquired images are first preprocessed for correcting geometric image distortion, segmenting and identifying 2-D image coordinates of the implants. Since we use the 2-D image coordinates of the identified implants, nonuniform intensity distortions do not affect the process according to this embodiment of the current invention. However, nonlinear geometric distortion in the image causes errors in the reconstruction by shifting the location of the 2-D projected implants. Thus, prior to reconstruction, geometric distortion correction of the image is performed. At the same time, calibration and pose tracking are performed to reconstruct a volume from images taken at arbitrary positions of the c-arm. In the calibration process, we determine intrinsic camera parameters of the c-arm (image pixel size and focal spot, i.e., the 3-D location of the x-ray source with respect to each image plane). Since the pixel size of the detector remains the same throughout the life of the c-arm, the c-arm calibration problem reduces to estimation of the focal spot. However, since the location of the focal spot varies as the pose of the c-arm changes, it should be computed from pose to pose at which each image is taken. In order to save time in the operating room, we perform the distortion parameter computation and calibration process only once. We mount a calibration fixture on the intensifier tube, and take a representative image within an expected range of the c-arm movement. Since we acquire images within a small angle variation range, the estimation errors do not critically affect the reconstruction result (A. K. Jain, R. Kon, Y. Zhou, and G. Fichtinger, "C-arm calibration—Is it really necessary?," *LNCS*, vol. 3749, pp. 639-646, 2005). The intrinsic camera parameters and the geometric dewarp parameters of the c-arm are estimated based on this image prior to the surgery. Although the intrinsic camera parameters of the c-arm can be determined before the surgery, the pose parameters (three parameters for rotation and three parameters for translation) of the c-arm are computed at each image acquisition pose by using external tracking devices such as optical tracker, encoder, and fluoroscope tracking radiographic fiducial structure such as (A. K. Jain, T. Mustafa, Y. Zhou, C. Burdette, G. S. Chirikjian, and G. Fichtinger, "FTRAC—A robust fluoroscope tracking fiducial," *Med. Phys.*, vol. 32, pp. 3185-3198, 2005).

In realistic scenarios when N radioactive seeds are implanted, several seeds are often overlapping in each projection such that only $N_i$ seed locations are identified in the ith image, where $N_i \leq N$. A seed-matching problem is constructed by thinking about matching the locations of N seeds rather than the seeds themselves. Accordingly, the seed localization can be formulated as the following assignment problem that is able to handle the hidden seed problem. For I ($\geq 3$) x-ray images, $$\min_{x_{i_1 i_2 i_3 \ldots i_I}} \sum_{i_1=1}^{N_1} \sum_{i_2=1}^{N_2} \sum_{i_3=1}^{N_3} \ldots \sum_{i_I=1}^{N_I} c_{i_1 i_2 i_3 \ldots i_I} x_{i_1 i_2 i_3 \ldots i_I} \quad (1)$$

s.t.

$$\sum_{i_2=1}^{N_2} \sum_{i_3=1}^{N_3} \ldots \sum_{i_I=1}^{N_I} x_{i_1 i_2 i_3 \ldots i_I} \geq 1, \quad \forall i_1 \quad (2)$$

$$\sum_{i_1=1}^{N_1} \sum_{i_3=1}^{N_3} \ldots \sum_{i_I=1}^{N_I} x_{i_1 i_2 i_3 \ldots i_I} \geq 1, \quad \forall i_2$$

$$\vdots$$

$$\sum_{i_1=1}^{N_1} \sum_{i_2=1}^{N_2} \ldots \sum_{i_{I-1}=1}^{N_{I-1}} x_{i_1 i_2 i_3 \ldots i_I} \geq 1, \quad \forall i_I$$

$$\sum_{i_1=1}^{N_1} \sum_{i_2=1}^{N_2} \sum_{i_3=1}^{N_3} \ldots \sum_{i_I=1}^{N_I} x_{i_1 i_2 i_3 \ldots i_I} = N$$

$$x_{i_1 i_2 i_3 \ldots i_I} \in \{0, 1\}, \quad \forall i_1, i_2, \ldots i_I$$

where $x_{i_1 i_2 \ldots i_I}$ is equal to one when the match $<i_1, i_2, \ldots, i_I>$ is chosen and is zero otherwise, and $c_{i_1 i_2 \ldots i_I}$ are the costs associated with the matches. Eq. (1) sums only over the identified seed locations in each image. It is therefore not necessary in this framework to try to "disambiguate" seed locations in order to arrive at N seeds in each image. The inequality constraints in the Eq. (2) are used instead of equalities in order to handle the occurrence of hidden seeds. These inequalities permit more than one assignment to each identified seed location in each image. (If that happens during optimization, then the "hidden seeds" have been automatically identified.) The equality constraint that appears in the Eq. (2) guarantees that exactly N seeds are matched. The above assignment problem can be stated in a very concise way. Let $N' = N_1 N_2 \ldots N_I$, and let $x \in \{0,1\}^{N'}$ and $c \in R^{N'}$ be vector forms of $x_{i_1 i_2 \ldots i_I}$ and $c_{i_1 i_2 \ldots i_I}$ in the Eq. (1), respectively. Let M be a matrix form of the inequality constraints in the Eq. (2). Then, the above problem can be formulated as the following binary integer program (BIP):

$$P: \text{minimize } c^T x \quad (3)$$

$$\text{s.t. } Mx \geq 1_I$$

$$x \cdot 1_{N'} = N \quad (4)$$

$$x \in \{0,1\}^{N'}$$

where $1_I = [1, 1, \ldots, 1]^T \in Z^I$ and $a \geq b$ means that, for every ith element, $a_i \geq b_i$. Since each element of x is either 0 or 1 and there must be N ones, Eq. (3) is equivalent to choosing N cost coefficients that minimize the overall cost while satisfying the Eq. (4).

Figure 2:
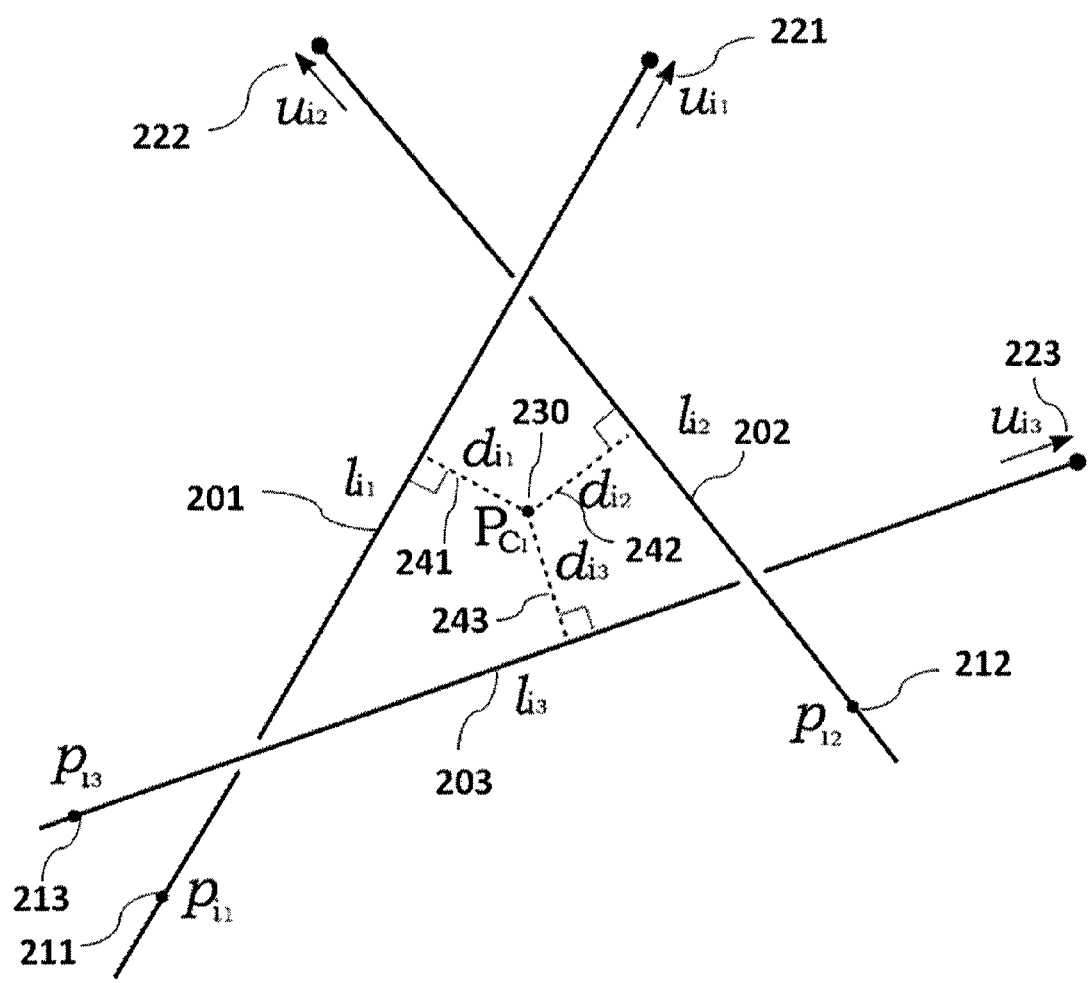
FIG. 2 shows an example of symbolic intersection and reconstruction accuracy cost computation for three images to illustrate some concepts of the current invention.

In order to fully specify the BIP in the Eqs. (3) and (4), the cost coefficients c must be specified. Among the various possible costs, reconstruction accuracy (RA) is used as a cost metric due to its simple geometric interpretation, speed of computation, and the utility in cost pruning. The basic idea of RA is as follows. Consider a proposed match comprising I seed locations from I different images. If the locations truly correspond to the same 3-D seed, then the I lines connecting their positions on the detectors with their corresponding x-ray source positions should intersect at the true 3-D seed position, and RA=0. The more likely situation, as illustrated in FIG. 2 for the case of I=3, is that the lines will "narrowly" miss each other due to calibration and pose errors. In this case, both the RA will be greater than zero but still small if calibration and pose errors are not too large. At the same time, if one or more lines do not correspond to the same 3-D seed as the other lines, then the estimated intersection will not, in general, be close to any line, and the RA will be large, which reflects a poor match. It is therefore understood that if RA is small—i.e., close to zero—the likelihood of these seeds correctly matching is high, while if RA is large, the likelihood of a correct seed match is small.

To arrive at a mathematical definition of RA, for I images, assume that there are $N_j$ identified seeds in image j with seed index $i_j = 1, 2, \ldots, N_j$. Let line $l_{ij}$ 201, 202, 203 be defined by the point $p_{ij}$ 211, 212, 213, e.g., the seed $i_j$ identified in the image j, and the unit direction $u_{ij} = (a_{ij}, b_{ij}, c_{ij})$ 221, 222, 223, as illustrated in FIG. 2. Let $C_I$ be a multi-index representing the combination $<i_1, i_2, \ldots, i_I>$. For each combination $C_I$, we define the estimated intersection point $P_{C_I}$ 230 of I lines as the point that minimizes the sum of the square distances from $P_{C_I}$ to the I lines 202. Then RA for the combination $C_I$ is defined as the root mean square distance from $P_{C_I}$ to each line, as follows $$RA(C_I) = \sqrt{\frac{1}{I} \sum_{j=1}^{I} d(P_{C_I}, l_{ij})^2}, \quad (5)$$

where $d(P_{C_I}, l_{ij})$ 241, 242, 243 is the Euclidean distance from $P_{C_I}$ 230 to line $l_{ij}$ 201, 202, 203. The best matches comprise lines passing close to a single estimated intersection point and are therefore those that minimize the $RA(C_I)$. It should be noted that we have specifically chosen the 2-norm rather than the 1-norm or $\infty$-norm because it permits fast computations, as we shall see. It is convenient to minimize the square of $RA(C_I)$, which we can write and expand as follows $$\mathcal{F} = RA(C_I)^2 = \frac{1}{I}\sum_{j=1}^{I}\|(P_{C_I} - p_{i_j}) \times u_{i_j}\|^2$$

$$= \frac{1}{I}\sum_{j=1}^{I}(P_{C_I} - p_{i_j})^T U_{i_j} U_{i_j}^T (P_{C_I} - p_{i_j}),$$

where $U_{ij}$ is a skew-symmetric matrix formed from the elements of $u_{ij}$ as follows $$U_{i_j} \triangleq \begin{bmatrix} 0 & -c_{i_j} & b_{i_j} \\ c_{i_j} & 0 & -a_{i_j} \\ -b_{i_j} & a_{i_j} & 0 \end{bmatrix}.$$

Since, by definition, $P_{C_I}$ achieves the minimum of the square of $RA(C_I)$, it can be analytically computed by solving $\nabla \mathcal{F}=0$ as $$P_{C_I} = \left[\sum_{j=1}^{I} A_{i_j}\right]^{-1} \left[\sum_{j=1}^{I} A_{i_j} p_{i_j}\right] \quad (6)$$

where $A_{ij}=U_{ij}U_{ij}^T$. Note that $P_{C_I}$ can be computed very efficiently by using just a few summations followed by a 3×3 matrix inversion. Once the correspondences are resolved, the 3-D locations of the N implanted seeds are declared to be the estimated intersection points $P_{C_I}$'s of all N matches.

Given I images each having N seeds (i.e., no hidden seeds), there are $N_i$ cost coefficients and $(N!)^{I-1}$ feasible solutions. Since the number of implanted seeds in prostate brachytherapy can be easily over 100 and at least three images are required for unique reconstruction, it is practically impossible to compute all the cost coefficients and consider every feasible solution. However, our optimization problem has a salient geometrical feature that we can exploit: the optimal solution has a near-zero cost when the pose error is small. We use this observation to reduce the number of variables in our problem, thus permitting us to get the optimal solution at reasonable computational complexity. Therefore, for a given feasible solution, all cost coefficients that are greater than the cost associated with this solution cannot be selected in the optimal solution. The cost associated with this solution therefore becomes a threshold on the cost of the optimal solution. Since those coefficients higher than this threshold can never be selected, the dimension of the problem can be reduced by removing those coefficients from further consideration. This means that the original problem P in Eqs. (3) and (4) is equivalent to the following problem of reduced dimensionality:

$$\tilde{P}: \text{minimize } \tilde{c}^T \tilde{x} \quad (7)$$

s.t. $\tilde{M}\tilde{x} \geq 1_I$ $\tilde{x} \cdot 1_K = N \quad (8)$ $\tilde{x} \in \{0,1\}^K$ where $\tilde{c} \in R^K$ ($K \leq N'$) and $\tilde{M}=MR$ with a dimensionality reduction matrix R such that $[x_{iI} \ldots 0 \ldots x_{ii} \ldots 0 \ldots x_{iK}]^T = R[\tilde{x}_1 \tilde{x}_2 \ldots \tilde{x}_K]^T$. Once the reduced problem $\tilde{P}$ is solved with a solution $\tilde{x}^*$, the optimal solution to the original problem P is simply given by $x^*=R\tilde{x}^*$. If the dimensionality reduction is sufficiently large, then the new problem can be solved exactly in reasonable time even though the original problem is far too costly to solve.

The dimensionality reduction approach described above requires the computation of only K cost coefficients that are lower than the threshold. But the important question is how one can efficiently determine whether a cost coefficient is higher than the threshold without actually computing it. The RA for any combination $C_I$ (when I images are used) obeys the following lower bound.

$$RA(C_I)^2 \geq \frac{1}{2I(I-1)} \sum_{j,k \in \{1,2,\ldots,I\}, \, k>j} d(l_{i_j}, l_{i_k})^2 \quad (9)$$

where $d(l_{ij}, l_{ik})$ is the Euclidean distance between lines $l_{ij}$ and $l_{ik}$ that originate from seeds $i_j$ and $i_k$ in images j and k with unit direction vectors $u_{ij}$ and $u_{ik}$, respectively. Eq. (9) provides the key for limiting our cost computations. We start by computing $d(l_{ij}, l^{ik})^2$ for all line pairs in all I images. Now consider the partial sums for the combination $C_m=\langle i_1, i_2, \ldots, i_m\rangle$ from the first m images defined by $$b(C_m) = \sum_{j,k \in \{1,2,\ldots,m\}, \, k>j} d(l_{i_j}, l_{i_k})^2, \quad (10)$$

which includes all line-pair distances among the $C_m$. This partial sum can be recursively computed for the first m images as follows:

$$b(C_m) = b(C_{m-1}) + \sum_{j=1}^{m-1} d(l_{i_j}, l_{i_m})^2. \quad (11)$$

We see that $b(C_m)$ is an increasing function and it is related to our RA bound [see Eq. (9)] in the following way: $RA(C_I)^2 \geq b(C_I)/(2I(I-1))$. This means that once $b(C_m)$ has achieved a certain threshold, say $\eta$, the RA of any possible matches that include the currently selected m lines must be larger than $\sqrt{\eta/(2I(I-1))}$. Accordingly, the computation of $b(C_I)$ is not necessary because the current collection of lines (from only images 1, . . . , m) cannot possibly be part of the solution. This property can be used in a recursive algorithm in which one image is added at each iteration and all coefficients that remain lower than $\eta$ are updated. Once all I images have been considered, the actual RA cost coefficients can be computed from the matches that remain below $\eta$, the dimensionality reduction threshold. This pruning approach is capable of culling a huge number of possible solutions and removing their cost computation from the overall computational workload.

The resulting reduced BIP is converted to a corresponding linear program (LP) and solved by a relaxed LP with a fractional constraint $x \in [0,1]^K$ instead of the binary constraint $x \in \{0,1\}^K$. The relaxed LP is solved by the interior-point method followed by a test to see if the solution is binary (up to numerical errors). It is well-known that linear programs can be solved optimally in polynomial time using the interior point method. If the solution of the LP with fractional constraints turns out to be binary, it is optimal for the BIP because its optimality is proven by the LP solver. However, for some cases, the solution of the LP is fractional (i.e., some elements of the solution x are not binary), and we must perform rounding of this fractional solution to get a binary solution. In such cases, we perform rounding under the assumption that the elements with higher fractional values in the solution are more likely to be 1. Therefore, we first sort the fractional solution in a descending order and the first N elements of the solution are rounded to 1.

Figure 3:
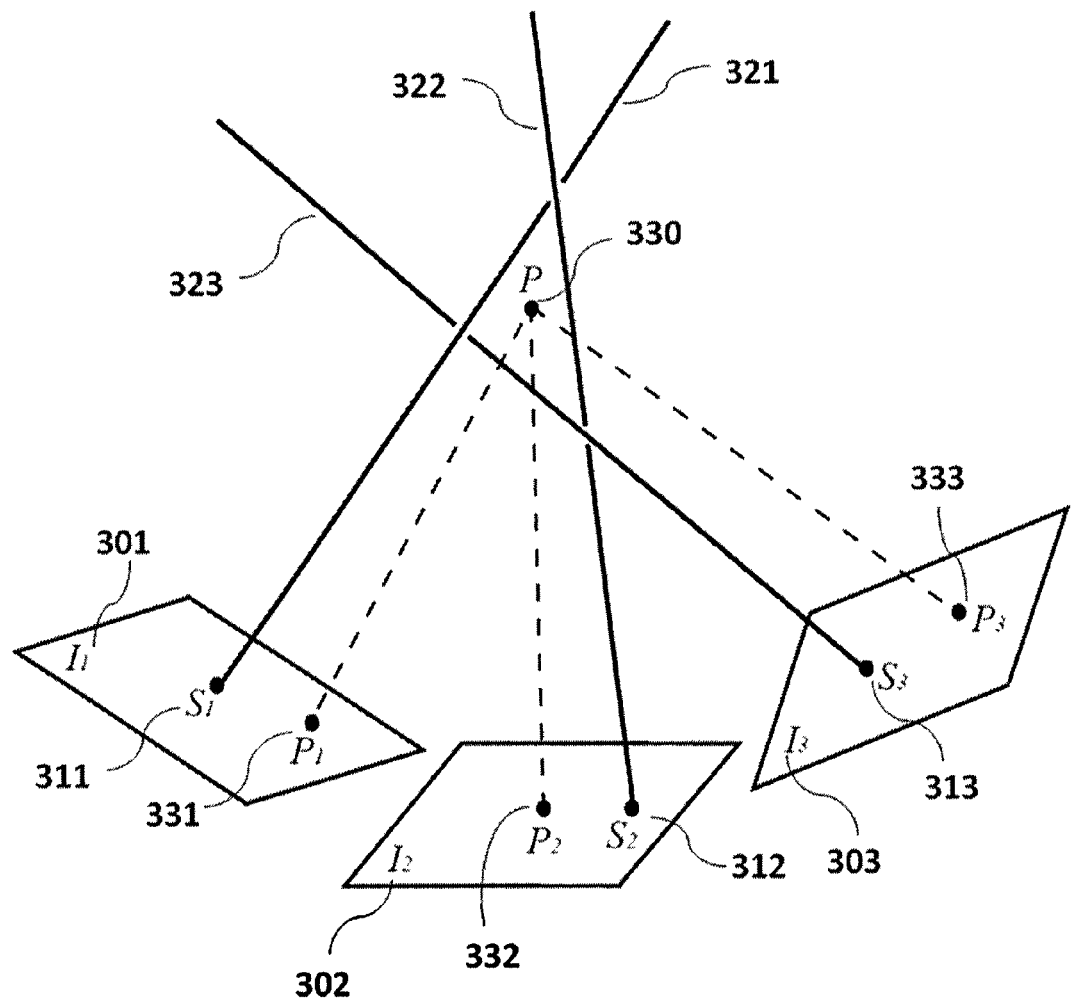
FIG. 3 shows an example of geometry for projection error computation for three images according to an embodiment of the current invention.

Once initial 3-D positions of the implants are computed with resolved correspondences, one can use these 3-D positions of the implants as point features to further correct the tracking errors. The image pose tracking errors could be significantly large depending on the performance of the tracking device especially when a non-encoded mobile c-arm is used. Additionally, patients may move during image acquisitions. Even though image pose errors and the amount of patient movements are small, they could noticeably affect the overall matching accuracy due to the small size of the implants and their large numbers. Both motions can be mathematically modeled as a rotation and a translation, and can be corrected by minimizing projection errors (PE, see FIG. 3). Since correspondences between the reconstructed 3-D implants and the 2-D implant images are already known, the overall cost function can be defined as a function of projection errors as $f(\delta x(R, T))$ where $\delta x(R, T)$ is the projection error between the measured implant coordinates 311, 312, 313 and the reprojected implant coordinates 331, 332, 333, of the reconstructed seed location 330, and R and T are the rotation and translation parameters, respectively. The erroneous R and T can be corrected by solving for the following minimization problem:

$$(\hat{R}, \hat{T}) = \operatorname*{argmin}_{R,T} f(\delta x(R, T)) \quad (12)$$

The seed matching and the motion compensation processes can be iteratively updated in an alternate way as necessary.

As the motion compensation process improves the c-arm pose, $\eta$ can be adaptively reduced because more accurate image poses result in smaller RA cost. Therefore, for every iteration, $\eta$ is reduced to $\eta = s \times \max c_{i_1 i_2 \ldots i_l}$ for $\{i_1, i_2, \ldots, i_l | x_{i_1 i_2 \ldots i_l} = 1\}$ where s is a scaling parameter that can be determined empirically, e.g., 2. By adaptively reducing $\eta$, larger dimensionality reduction can be achieved, thus yielding reduced computation time in successive iterations. At the same time, this process is much faster than use of a lesser dimensionality reduction factor and still has a high probability of yielding a binary solution that is globally optimal.

Figure 4:
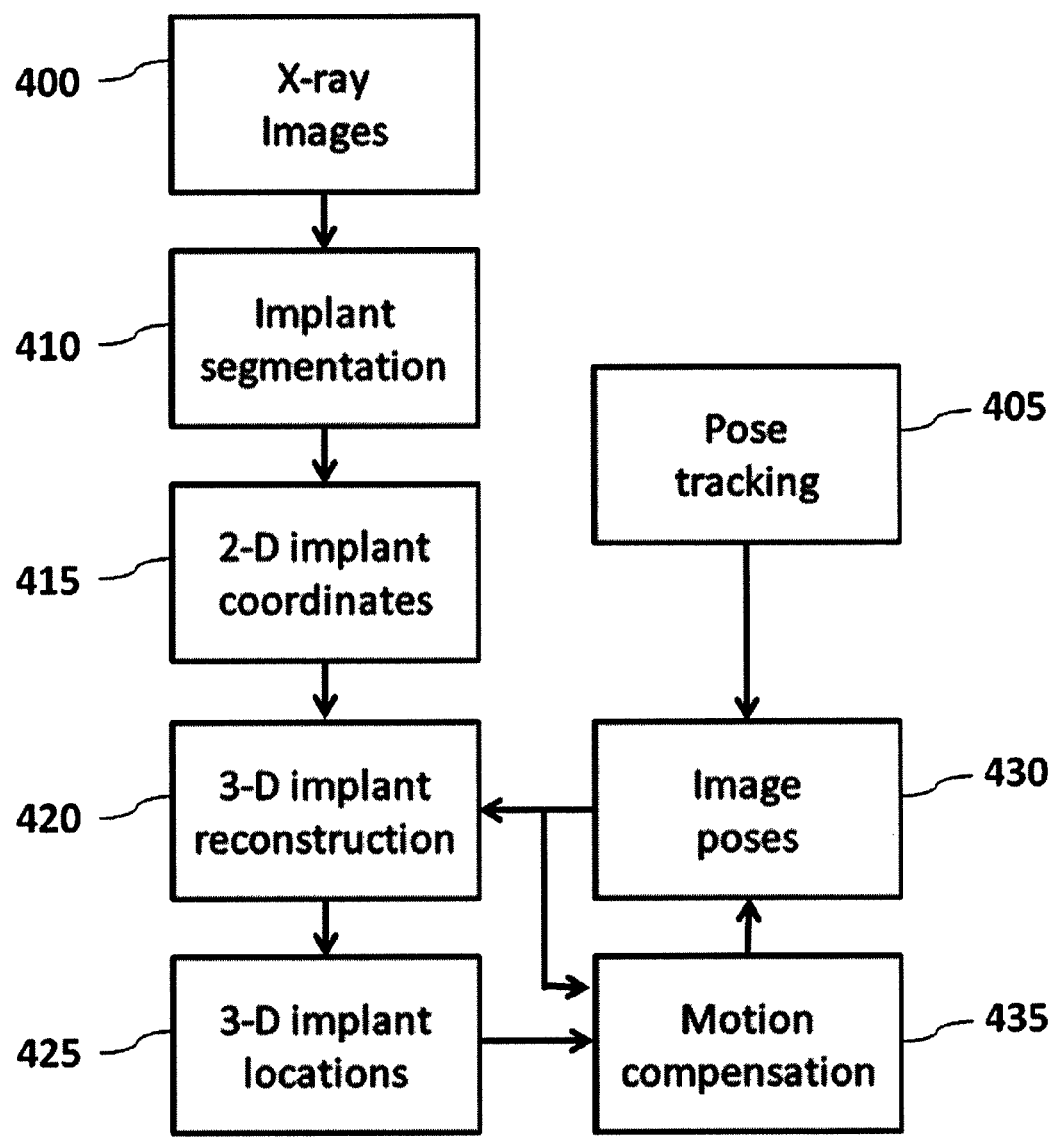
FIG. 4 is a block diagram describing an implant localization process with motion compensation according to an embodiment of the current invention.

Finally, FIG. 4 depicts the overall process of implant localization according to an embodiment of the current invention. When the surgeon needs to evaluate and validate the implant process, x-ray images 400 are acquired at three different positions, and preprocessed for geometric image distortion correction. The implants are then segmented 410 from the acquired images to get binary images of the implants, and 2-D image coordinates of the implants 415 are identified. The x-ray source is tracked 405 by a tracking device and pose of each image is computed 430. Three-dimensional location of the implants are computed 420 from the computed 2-D image coordinates of the implants in every image and the corresponding image poses by solving the combinatorial optimization problem. The initially reconstructed implant locations and their correspondences 425 are used as a fiducial for correcting the errors in the image poses 435, 430. The 3-D implant reconstruction 420 and motion compensation 435 are repeated in an alternate way.

The methods described herein exploit the signature of x-ray beam attenuation produced by solid objects (i.e., seeds or markers) inside the material being imaged. It will be appreciated that the methods may be applied to any clinical application where small x-ray opaque objects are present or a set of point features can be extracted from target objects, wherein real-time 3-D reconstruction of the target from c-arm fluoroscopy and its registration to other imaging modalities (such as, for example, US, CT, or MRI) or to statistical anatomical atlases are required. For example, localization of a surgical tool from minimal number of x-ray images and its registration to the surgical volume provided by CT or MRI.

Embodiments described may be implemented in a system including computer hardware, such as a computer-based system for use with imaging modalities to combine images from the imaging technologies and registration of markers or seeds common to the images of the two modalities. The system may further include hardware associated with one or more imaging modalities, such as, for example, an ultrasound device, an x-ray (e.g., fluoroscopy, CT), an MRI device, or a device related to a pre-implant plan of the material being imaged.

As described in examples above, an embodiment of the present invention is directed to 3-D reconstruction and localization of radioactive implants from a limited number of x-ray images for the purposes of providing real-time monitoring and optimization of radiation implant procedures. An advantage of some embodiments of the present invention can include the ability of localizing radioactive implants from a minimum number (e.g., 3-4) of x-ray images. Some embodiments can provide the ability to automatically handle hidden seed problems where one implant overlaps with another implant in the projection resulting in unequal number of identified implants in every image. Some embodiments of the present invention formulate the reconstruction and localization problem as a combinatorial optimization that is constrained to resolve the hidden seed problem. Some embodiments of the present invention can provide robustness of the localization process to errors in image pose tracking, calibration, and segmentation. Since methods according to some embodiments of the present invention solve a global optimization problem, it is much more robust to various errors than other currently available methods which tackle this problem in approximate ways for efficiency. Another aspect of some embodiments of the present invention is the efficient computation of the cost metric and dimensionality reduction through a pruning process that significantly reduces the size of the original optimization problem and enables real-time reconstruction. Another aspect of some embodiments of the present invention is the ability of correcting errors caused from tracking and by patient motion. It utilizes the reconstructed implants as a point fiducial and iteratively solves for the 3-D reconstruction and motion compensation.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of processing image data from an imaging system for locating a plurality N of objects embedded in a body, comprising:

receiving data for a first two-dimensional image of a region of interest of said body containing said plurality N of objects, said first two-dimensional image being obtained from a first imaging setting of said imaging system relative to said region of interest;

receiving data for a second two-dimensional image of a region of interest of said body containing said plurality N of objects, said second two-dimensional image being obtained from a second imaging setting of said imaging system relative to said region of interest;

receiving data for a third two-dimensional image of a region of interest of said body containing said plurality N of objects, said third two-dimensional image being obtained from a third imaging setting of said imaging system relative to said region of interest;

determining two-dimensional positions for a first plurality of objects $N_1$ in said first two-dimensional image, each of said first plurality of objects $N_1$ corresponding to at least one of said plurality N of objects;

determining two-dimensional positions for a second plurality of objects $N_2$ in said second two-dimensional image, each of said second plurality of objects $N_2$ corresponding to at least one of said plurality N of objects;

determining two-dimensional positions for a third plurality of objects $N_3$ in said third two-dimensional image, each of said third plurality of objects $N_3$ corresponding to at least one of said plurality N of objects;

calculating a cost associated with each of said first plurality of objects $N_1$ paired with each of said second plurality of objects $N_2$ to provide $N_1 \times N_2$ pair combinations, each said cost being indicative of a likelihood of a correct pairing;

eliminating some of said $N_1 \times N_2$ pair combinations from further calculations based on a predetermined threshold to result in a reduced number $n_1$ of remaining pairs for further calculations, $n_1$ being less than $N_1 \times N_2$;

calculating a cost associated with each of said $n_1$ pairs and each of said third plurality of objects $N_3$ to provide $n_1 \times N_3$ triplet combinations, each said cost being indicative of a likelihood of a correct triplet matching;

eliminating some of said $n_1 \times N_3$ triplet combinations from further calculations based on said predetermined threshold to result in a reduced number $n_2$ of remaining triplets, $n_2$ being less than $n_1 \times N_3$; and calculating three-dimensional positions of each of said plurality N of objects embedded in said region of interest of said body based on surviving matches of objects in each said two-dimensional image, wherein said first, second and third imaging settings all are different from each other.

2. A method of processing image data according to claim 1, further comprising:

receiving data for a fourth two-dimensional image of a region of interest of said body containing said plurality N of objects, said fourth two-dimensional image being obtained from a fourth imaging setting of said imaging system relative to said region of interest;

determining two-dimensional positions for a fourth plurality of objects $N_4$ in said fourth two-dimensional image, each of said fourth plurality of objects $N_4$ corresponding to at least one of said plurality N of objects;

calculating a cost associated with each of said $n_2$ triplets and each of said fourth plurality of objects $N_4$ to provide $n_2 \times N_4$ quartet combinations, each said cost being indicative of a likelihood of a correct quartet matching;

eliminating some of said $n_2 \times N_4$ triplet combinations from further calculations based on said predetermined threshold to result in a reduced number $n_3$ of remaining quartets, $n_3$ being less than $n_2 \times N_4$; and calculating three-dimensional positions of each of said plurality N of objects embedded in said region of interest of said body based on surviving matches of objects in each said two-dimensional images, wherein said first, second, third and fourth imaging settings all are different from each other.

3. A method of processing image data according to claim 1, wherein said threshold is selected based on known properties of said imaging system.

4. A method of processing image data according to claim 3, wherein said known properties of said imaging system include known measurement precision.

5. A method of processing image data according to claim 3, wherein said known properties of said imaging system include positioning precision.

6. A method of processing image data according to claim 1, wherein said cost is a function of distance of closest approach of lines extending from a corresponding two-dimensional position to an imaging source direction.

7. A method of processing image data according to claim 1, wherein said imaging system is an x-ray imaging system.

8. A method of processing image data according to claim 7, wherein said plurality N of objects are radiotherapy seeds implanted in a patient.

9. A method of processing image data according to claim 1, wherein said plurality N of objects are at least N=10 objects.

10. A method of processing image data according to claim 1, wherein said plurality N of objects are at least N=100 objects.

11. A method of processing image data according to claim 1, wherein said calculating three-dimensional positions of each of said plurality N of objects embedded in said region of interest of said body is performed sufficiently fast to provide real time results to a doctor providing a surgical procedure.

12. A method of processing image data according to claim 1, further comprising:

assigning said calculated three-dimensional positions of each of said plurality N of objects embedded in said region of interest of said body as fiducial positions, receiving data for at least one subsequent two-dimensional image of said region of interest of said body containing said plurality N of objects subsequent to said assigning;

determining two-dimensional positions of at least some of said plurality of objects N in each of said at least one subsequent two-dimensional image;

projecting each of said fiducial positions onto each of said at least one subsequent two-dimensional image to determine expected positions of each of said plurality of objects N therein; and determining corrections to tracking error of said imaging system or a patient motion of said region of interest so that the expected position of each plurality of objects match to two-dimensional positions of corresponding plurality of objects in each two-dimensional image.

13. A non-transitory computer-readable medium comprising software for processing image data from an imaging system for locating a plurality N of objects embedded in a body, which software when executed by a computer causes the computer to:

receive data for a first two-dimensional image of a region of interest of said body containing said plurality N of objects, said first two-dimensional image being obtained from a first imaging setting of said imaging system relative to said region of interest;

receive data for a second two-dimensional image of a region of interest of said body containing said plurality N of objects, said second two-dimensional image being obtained from a second imaging setting of said imaging system relative to said region of interest;

receive data for a third two-dimensional image of a region of interest of said body containing said plurality N of objects, said third two-dimensional image being obtained from a third imaging setting of said imaging system relative to said region of interest;

determine two-dimensional positions for a first plurality of objects $N_1$ in said first two-dimensional image, each of said first plurality of objects $N_1$ corresponding to at least one of said plurality N of objects;

determine two-dimensional positions for a second plurality of objects $N_2$ in said second two-dimensional image, each of said second plurality of objects $N_2$ corresponding to at least one of said plurality N of objects;

determine two-dimensional positions for a third plurality of objects $N_3$ in said third two-dimensional image, each of said third plurality of objects $N_3$ corresponding to at least one of said plurality N of objects;

calculate a cost associated with each of said first plurality of objects $N_1$ paired with each of said second plurality of objects $N_2$ to provide $N_1 \times N_2$ pair combinations, each said cost being indicative of a likelihood of a correct pairing;

eliminate some of said $N_1 \times N_2$ pair combinations from further calculations based on a predetermined threshold to result in a reduced number $n_1$ of remaining pairs for further calculations, $n_1$ being less than $N_1 \times N_2$;

calculate a cost associated with each of said $n_1$ pairs and each of said third plurality of objects $N_3$ to provide $n_1 \times N_3$ triplet combinations, each said cost being indicative of a likelihood of a correct triplet matching;

eliminate some of said $n_1 \times N_3$ triplet combinations from further calculations based on said predetermined threshold to result in a reduced number $n_2$ of remaining triplets, $n_2$ being less than $n_1 \times N_3$; and calculate three-dimensional positions of each of said plurality N of objects embedded in said region of interest of said body based on surviving matches of objects in each said two-dimensional image, wherein said first, second and third imaging settings all are different from each other.

14. A non-transitory computer-readable medium comprising software according to claim 13, wherein said imaging system is an x-ray imaging system.

15. A non-transitory computer-readable medium comprising software according to claim 14, wherein said plurality N of objects are radiotherapy seeds implanted in a patient.

16. An imaging system for locating a plurality N of objects embedded in a body, comprising:

an illumination system;

a detection system arranged to form two-dimensional images of a region of interest containing said plurality N of objects embedded in said body; and a data processor encoded with software for processing image data from a detection system, wherein said software, when executed by a computer, causes the computer to:

receive data for a first two-dimensional image of a region of interest of said body containing said plurality N of objects, said first two-dimensional image being obtained from a first imaging setting of said imaging system relative to said region of interest;

receive data for a second two-dimensional image of a region of interest of said body containing said plurality N of objects, said second two-dimensional image being obtained from a second imaging setting of said imaging system relative to said region of interest;

receive data for a third two-dimensional image of a region of interest of said body containing said plurality N of objects, said third two-dimensional image being obtained from a third imaging setting of said imaging system relative to said region of interest;

determine two-dimensional positions for a first plurality of objects $N_1$ in said first two-dimensional image, each of said first plurality of objects $N_1$ corresponding to at least one of said plurality N of objects;

determine two-dimensional positions for a second plurality of objects $N_2$ in said second two-dimensional image, each of said second plurality of objects $N_2$ corresponding to at least one of said plurality N of objects;

determine two-dimensional positions for a third plurality of objects $N_3$ in said third two-dimensional image, each of said third plurality of objects $N_3$ corresponding to at least one of said plurality N of objects;

calculate a cost associated with each of said first plurality of objects $N_1$ paired with each of said second plurality of objects $N_2$ to provide $N_1 \times N_2$ pair combinations, each said cost being indicative of a likelihood of a correct pairing;

eliminate some of said $N_1 \times N_2$ pair combinations from further calculations based on a predetermined threshold to result in a reduced number $n_1$ of remaining pairs for further calculations, $n_1$ being less than $N_1 \times N_2$;

calculate a cost associated with each of said $n_1$ pairs and each of said third plurality of objects $N_3$ to provide $n_1 \times N_3$ triplet combinations, each said cost being indicative of a likelihood of a correct triplet matching;

eliminate some of said $n_1 \times N_3$ triplet combinations from further calculations based on said predetermined threshold to result in a reduced number $n_2$ of remaining triplets, $n_2$ being less than $n_1 \times N_3$; and calculate three-dimensional positions of each of said plurality N of objects embedded in said region of interest of said body based on surviving matches of objects in each said two-dimensional image, wherein said first, second and third imaging settings all are different from each other.

17. An imaging system according to claim 16, wherein said illumination system comprises an x-ray source and said detection system comprises an x-ray imaging detector.

* * * * *